US012577595B2

(12) United States Patent
Kabir et al.

(10) Patent No.: US 12,577,595 B2
(45) Date of Patent: Mar. 17, 2026

(54) METHOD FOR PREPARING A FATTY AMIDOALKYLDIALKYLAMINE

(71) Applicant: SPECIALTY OPERATIONS FRANCE, Lyons (FR)

(72) Inventors: Hocine Kabir, Communay (FR); Cinthia Nakamura, Sao Paulo (BR); Paula Delgado, Sao Paulo (BR); Fernanda Hoelscher, Barão Geraldo (BR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 554 days.

(21) Appl. No.: 17/923,517

(22) PCT Filed: Apr. 20, 2021

(86) PCT No.: PCT/EP2021/060282

§ 371 (c)(1), (2) Date: Nov. 4, 2022

(87) PCT Pub. No.: WO2021/239335

PCT Pub. Date: Dec. 2, 2021

(65) Prior Publication Data

US 2023/0183763 A1 Jun. 15, 2023

(30) Foreign Application Priority Data

May 26, 2020 (EP) .................................... 20176463

(51) Int. Cl.
*C12P 13/02* (2006.01)
*C12N 11/087* (2020.01)

(52) U.S. Cl.
CPC ............ *C12P 13/02* (2013.01); *C12N 11/087* (2020.01); *C12Y 301/01003* (2013.01)

(58) Field of Classification Search
CPC ................... C12P 13/02; C12N 11/087; C12Y 301/01003
See application file for complete search history.

(56) References Cited

U.S. PATENT DOCUMENTS

| | | | | |
|---|---|---|---|---|
| 5,973,203 | A | 10/1999 | Egraz et al. | |
| 2014/0050687 | A1 | 2/2014 | Burk et al. | |
| 2019/0300916 | A1* | 10/2019 | Clendennen | C12P 13/02 |

FOREIGN PATENT DOCUMENTS

| | | | |
|---|---|---|---|
| EP | 0298796 | A1 | 1/1989 |
| EP | 2818155 | A1 | 12/2014 |
| FR | 2757180 | A1 | 6/1998 |
| JP | H05-153985 | A | 6/1993 |
| KR | 101861785 | B1 | 5/2018 |
| WO | 9014429 | A1 | 11/1990 |
| WO | 98/47860 | A1 | 10/1998 |
| WO | 16064620 | A1 | 4/2016 |
| WO | 2018/081221 | A1 | 5/2018 |

OTHER PUBLICATIONS

Korupp, C., et al. "Scaleup of lipase-catalyzed polyester synthesis." Organic Process Research & Development 14.5 (2010): 1118-1124. (Year: 2010).*

De Meneses, Alessandra Cristina, et al. "Benzyl butyrate esterification mediated by immobilized lipases: Evaluation of batch and fed-batch reactors to overcome lipase-acid deactivation." Process Biochemistry 78 (2019): 50-57. (Year: 2019).*

Liu, Kuan Ju, Ahindra Nag, and Jei-Fu Shaw. "Lipase-catalyzed synthesis of fatty acid diethanolamides." Journal of agricultural and food chemistry 49.12 (2001): 5761-5764 (Year: 2001).*

Fernández-Pérez, Mónica, and Cristina Otero. "Selective enzymatic synthesis of amide surfactants from diethanolamine." Enzyme and microbial technology 33.5 (2003): 650-660. (Year: 2003).*

International Search Report issued in Application No. PCT/EP2021/060282, mailed on Jul. 2, 2021 (4 pages).

Written Opinion issued in International Application No. PCT/EP2021/060282, mailed on Jul. 2, 2021 (6 pages).

M. Quirós et al., "Lipase-Catalyzed Synthesis of Optically Active Amides in Organic Media", Tetrahedron: Asymmetry, 1993, vol. 4, No. 6, pp. 1105-1112 (8 pages).

K. J. Liu et al., "Lipase-Catalyzed Synthesis of Fatty Acid Diethanolamides", Journal of Agricultural and Food Chemistry, 2001, vol. 49, No. 12, pp. 5761-5764 (4 pages).

* cited by examiner

*Primary Examiner* — Robert J Yamasaki
*Assistant Examiner* — Trevor Kane
(74) *Attorney, Agent, or Firm* — Osha Bergman Watanabe & Burton LLP

(57) ABSTRACT

The present invent ion concerns a method for preparing a fatty amidoalkyldialkylamine by reacting a fatty acid with a dialkylaminoalkylamine, using a molar ratio of said dialkylaminoalkylamine to said fatty acid of more than 1 and up to 1.5, in the presence of *Candida antarctica* lipase as catalyst.

19 Claims, No Drawings

METHOD FOR PREPARING A FATTY AMIDOALKYLDIALKYLAMINE

The present application is a U.S. national stage entry under U.S.C. § 371 of International Application No. PCT/EP2021/060282 filed Apr. 20, 2021, which claims priority filed on 26 May 2020 in EUROPE with Nr 20176463.6, the whole content of these applications being incorporated herein by reference for all purposes.

The present invention concerns a method for preparing a fatty amidoalkyldialkylamine by enzymatic synthesis.

Fatty amidoalkyldialkylamines such as for example lauramidopropyl dimethylamine are well known chemical compounds which are widely used in industry in particular as intermediate compounds for the preparation of betaines and sultaines which are extensively used in personal care, home care and agrochemical compositions.

Fatty amidoalkyldialkylamines are commonly prepared by pure chemical route, as described for example in WO 98/47860 which discloses a method for producing carboxylic amides by reacting a carboxylic acid and amine. The reaction is performed under nitrogen, at high temperatures (about 180° C. or above).

There is a continuous need for providing new methods for preparing these useful chemical materials, which bring improvements in terms of efficiency, costs and environmental impact.

The inventors of the present application have now discovered that fatty amidoalkyldialkylamines could be prepared in an efficient manner by reacting a fatty acid with a dialkylaminoalkylamine in the presence of a particular enzyme as catalyst.

The present invention thus concerns a method for preparing at least one fatty amidoalkyldialkylamine by reacting at least one fatty acid containing from 8 to 24 carbon atoms with at least one dialkylaminoalkylamine of formula (I):

(I)

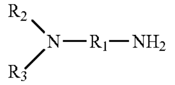

in which: $R_1$ represents a divalent alkyl group containing from 2 to 6 carbon atoms; $R_2$ and $R_3$ represent, independently of each other, monovalent alkyl groups containing from 1 to 4 carbon atoms, using a molar ratio of said dialkylaminoalkylamine to said fatty acid of more than 1 and up to 1.5, in the presence of *Candida antarctica* lipase as catalyst.

The present invention provides an enzymatic route for synthetizing fatty amidoalkyldialkylamines which leads to excellent yields, while requiring lower excess of the dialkylaminoalkylamine starting material and therefore consuming fewer amounts if this product and generating less effluents.

The synthesis can also be performed in milder conditions, in particular at lower temperatures, when compared to the prior art pure chemical routes and therefore allows significant energy savings (such as about 45%).

Other subjects, characteristics, aspects and advantages of the invention will emerge even more clearly on reading the description and the examples that follow.

In the present description, and unless otherwise indicated:

the expression "at least one" is equivalent to the expression "one or more" and can be replaced therewith;

the expression "between" is equivalent to the expression "ranging from" and can be replaced therewith and implies that the limits of the range are included;

the term "compound in CX" designates in a manner known per se a compound having X atoms of carbon in its molecule.

The Starting Materials:

The method of the invention uses two starting materials as described below.

The first starting material is a fatty acid having 8 to 24 carbon atoms.

Such compound corresponds to the general formula R—COOH with R representing a linear or branched, saturated or unsaturated hydrocarbon group containing from 7 to 23 carbon atoms.

Fatty acids wherein the R group is linear, saturated or unsaturated, are preferred.

Preferred fatty acids are those containing from 10 to 20 and more preferably from 12 to 18 carbon atoms.

Particularly preferred fatty acids are lauric acid, stearic acid, oleic acid, and mixtures thereof, as well as mixtures of fatty acids comprising from 8 to 18 carbon atoms and preferably from 12 to 18 carbon atoms.

Lauric acid and stearic acid are particularly preferred.

The second starting material is a dialkylaminoalkylamine of formula (I):

(I)

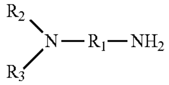

$R_1$ represents a divalent alkyl group containing from 2 to 6 carbon atoms, preferably 3 or 4 carbon atoms and most preferably 3 carbon atoms which corresponds to $R_1$ representing a propyl group.

$R_2$ and $R_3$ may be identical or different and represent monovalent alkyl groups containing from 1 to 4 carbon atoms, preferably 1 or 2 carbon atoms.

According to a preferred embodiment, the $R_2$ and $R_3$ groups are identical, and preferably represent methyl or ethyl groups, most preferably $R_2$ and $R_3$ both represent methyl groups.

According to a most preferred embodiment, the dialkylaminoalkylamine of formula (I) is dimethylaminopropyl amine, which corresponds to $R_1$ representing a propyl group and $R_2$ and $R_3$ both representing methyl groups.

In the present invention, these two starting materials are combined with a molar ratio of said dialkylaminoalkylamine to said fatty acid of more than 1, that is to say strictly greater than 1.

The molar ratio preferably ranges from 1.05 to 1.3, and most preferably from 1.1 to 1.2.

The Fatty Amidoalkyldialkylamines:

The present invention provides an improved method of synthesis of fatty amidoalkyldialkylamines having the general formula (II):

(II)

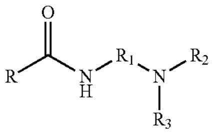

with R, $R_1$, $R_2$ and $R_3$ having the definitions given above, including the preferred embodiments described above.

A particularly preferred compound of formula (II) is lauramidopropyl dimethylamine, which corresponds to R being a linear alkyl group in $C_{11}$, $R_1$ being a propyl group and $R_2$ and $R_3$ both being methyl groups. This compound is obtained by reacting lauric acid and dimethylaminopropylamine as starting materials, according to the following reaction scheme:

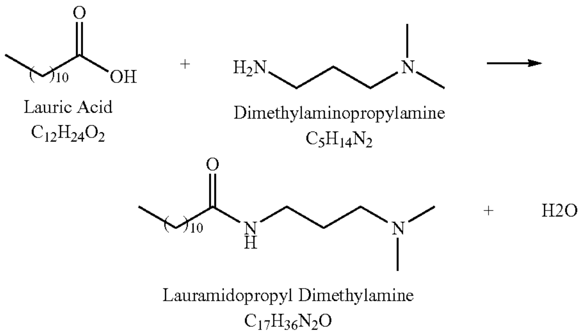

Lauric Acid $C_{12}H_{24}O_2$

Dimethylaminopropylamine $C_5H_{14}N_2$

Lauramidopropyl Dimethylamine $C_{17}H_{36}N_2O$

Other preferred compounds are amidopropyl dimethylamines obtained from stearic acid, oleic acid, as well as from mixtures of fatty acids comprising from 8 to 18 carbon atoms and preferably from 12 to 18 carbon atoms.

The Enzyme Catalyst:

The present invention uses a specific lipase, namely *Candida antarctica* lipase, as catalyst.

The catalyst is preferably under the form of a solid catalyst containing *Candida Antarctica* lipase grafted onto a polymeric support, preferably an anionic resin such as an acrylic resin.

Such catalysts made of enzymes grafted onto appropriate solid supports are well known in the art and commercially available.

A particular commercial catalyst which can be used in the present invention contains *Candida Antarctica* lipase in an amount of 21% by weight, grafted onto an acrylic resin and is sold under the name Novozym 435 by the company Novozymes.

The catalyst is preferably used in an amount ranging from 0.2 to 2% by weight, preferably from 0.5 to 1.5% by weight, and most preferably in an amount of 0.9 to 1.1% by weight, with regard to the total weight of fatty acid(s).

The above amounts correspond to the amount of catalyst active matter, ie the amount of *Candida antarctica* lipase. Such amounts do not include the possible support which is inert.

According to a preferred embodiment, *Candida Antarctica* lipase is the sole catalyst used in the process of the invention.

The Operating Conditions:

The reaction between the fatty acid(s) and the dialkylaminoalkylamine(s) is advantageously carried out at a temperature within the range from 75 to 120° C., preferably from 85 to 105° C., and most preferably from 90 to 100° C.

The reaction is preferably carried out under vacuum, at a pressure ranging from $25 \cdot 10^2$ to $200 \cdot 10^2$ Pa (25 to 200 mbar) preferably from $50 \cdot 10^2$ to $100 \cdot 10^2$ Pa (50 to 100 mbar).

The reaction is preferably carried out in a batch reactor, as described hereafter. The fatty acid(s) is (are) first loaded into the rector and the catalyst is added. The fatty acid(s) can be melted before being introduced into the reactor, or it(they) can be melted directly within the reactor, preferably before adding the catalyst. The mixture is heated up to the reaction temperature and placed under vacuum, and the dialkylaminoalkylamine(s) is(are) then added progressively with continuous mechanical stirring of the reaction medium.

The reaction is generally completed within a few hours, ranging from 8 to 40 hours, preferably from 15 to 30 hours.

In these conditions, the molar rate of conversion of fatty acid into fatty amidoalkyldialkylamines is advantageously above 99%, such as about 99.5% or even more—

At the end of the reaction, the agitation is turned off and the enzymatic catalyst is separated by decantation or filtration. Alternatively, the catalyst can be separated by centrifugation.

According to a preferred embodiment, after a first reaction cycle the catalyst is recycled to the reactor where it is reused for the next reaction batch. The catalyst can advantageously be recycled at least three times and up to twenty times, preferably up to ten times.

The fatty amidoalkyldialkylamine is then recovered. When the reaction is performed under vacuum, water and residual amine have already been removed from the reactor, and there is no need of further purification.

The examples of implementation of the invention below are given purely by way of illustration and shall not be interpreted at limiting the scope thereof.

EXAMPLES

Example 1: Synthesis of Lauramidopropyldimethylamine by Reacting Lauric Acid with Dimethylaminopropylamine The syntheses were carried out in a jacketed reactor having a volume of 250 mL coupled with a vacuum pump, a condenser, a mechanic stirrer and a peristaltic pump for amine feeding.

The reactions were performed at 95° C., under vacuum at 50-100 mbar, mechanical agitation, and with a fed-batch of amine. First, the lauric acid was introduced into the reactor. It can be melted in the reactor or be melted previously to the addition. Then, the enzymatic catalyst was added. The catalyst used was the commercial product Novozym 435 which contains 21% by weight of *Candida Antarctica* lipase originating from *Candida Antarctica* B, grafted onto an acrylic resin.

The amount of enzyme (active matter, ie excluding the support) used corresponds to 1% w/w based on lauric acid.

The stoichiometric amount of dimethylaminopropylamine (DMAPA) plus 10% of excess was added continuously into the reactor for a period of 7 hours. After 7 hours of feeding, the acid index was monitored for each hour. When it became constant, amine excess was added, divided into portions of 1%.

For the first reaction batch, a rate of 99.5% of conversion was achieved with 11% (molar) of amine excess. The total reaction time was around 15 hours.

After the reaction, the agitation was turned off for the enzymatic catalyst to go to the bottom of the reactor. The product was removed from the top. Acid index and residual amine were measured to certify that all specifications were achieved.

After removal of the product (end of cycle 1), a new reaction cycle was performed using the catalyst remaining in the reactor: a new charge of lauric acid was added, and the feeding of dimethyl aminopropylamine was started. Three successive reaction cycles were achieved using the same load of catalyst.

The table hereunder summarizes the conditions and results of the reaction for the three successive cycles.

| | Cycle 1 | Cycle 2 | Cycle 3 |
|---|---|---|---|
| Amount of lauric acid (g) | 113.65 | 113.65 | 113.64 |
| Amount of lauric acid (mol) | 0.57 | 0.57 | 0.57 |
| Amount of DMAPA (g) | 64.25 | 65.35 | 65.78 |
| Amount of DMAPA (mol) | 0.63 | 0.64 | 0.64 |
| Excess of amine vs stoechiometric amount (mol %) | 11 | 12.3 | 12.3 |
| Mass of Novozym 435(*) catalyst (g) | 5.77 | 5.77 (recycled) | 5.77 (recycled) |
| Reaction time (h) | 15 | 21 | 30.5 |
| Final acid index (mg kOH/g) | 0.83 | 0.54 | 0.73 |
| Free fatty acid remaining (% by weight) | 0.32 | 0.21 | 0.28 |
| Conversion (%) | 99.54 | 99.7 | 99.59 |

(*)contains 21% by weight of *Candida Antarctica* lipase

Example 2: Synthesis of Stearamidopropyldimethylamine by Reacting Stearic Acid with Dimethylaminopropylamine The synthesis was carried out in a jacketed reactor having a volume of 250 mL coupled with a vacuum pump, a condenser, a mechanic stirrer and a peristaltic pump for amine feeding.

The reaction was performed at 95° C., under vacuum at 50-100 mbar, mechanical agitation, and with a fed-batch of amine. First, the stearic acid was introduced into the reactor. It can be melted in the reactor or be melted previously to the addition. Then, the enzymatic catalyst was added. The catalyst used was the commercial product Novozym 435 which contains 21% by weight of *Candida Antarctica* lipase originating from *Candida Antarctica* B, grafted onto an acrylic resin.

The amount of enzyme (active matter, ie excluding the support) used corresponds to 1% w/w based on lauric acid.

The stoichiometric amount of dimethylaminopropylamine (DMAPA) plus 10% of excess was added continuously into the reactor for a period of 7 hours. After 7 hours of feeding, the acid index was monitored for each hour. When it became constant, amine excess was added, divided into portions of 1%.

A rate of 99.2% of conversion was achieved with 18% (molar) of amine excess. The total reaction time was around 20 hours.

After the reaction, the agitation was turned off for the enzymatic catalyst to go to the bottom of the reactor. The product was removed from the top. Acid index and residual amine are measured to certify that all specifications were achieved.

The table hereunder summarizes the conditions and results of the reaction for the synthesis.

| | |
|---|---|
| Amount of stearic acid (g) | 129.39 |
| Amount of stearic acid (mol) | 0.45 |
| Amount of DMAPA (g) | 54.74 |
| Amount of DMAPA (mol) | 0.54 |
| Excess of amine vs stoechiometric amount (mol %) | 20 |

-continued

| | |
|---|---|
| Mass of Novozym 435(*) catalyst (g) | 6.46 |
| Reaction time (h) | 20 |
| Final acid index (mg kOH/g) | 1.16 |
| Free fatty acid remaining (% by weight) | 0.45 |
| Conversion (%) | 99.2 |

(*)contains 21% by weight of *Candida Antarctica* lipase

The examples above show that the method of the invention provides an efficient route for the synthesis of fatty amidoalkyldialkylamines.

The benefits of the enzymatic process of the invention in particular versus chemical synthesis are the reduction of dialkylaminoalkylamine raw material from 30 to 10-13% and the reduction of the temperature. Both parameters have a significant impact on the process costs.

Furthermore in the chemical synthesis, after specifying acidity content, another step is required in order to remove residues of DMAPA, which is not needed in the method of the invention.

The invention claimed is:

1. A method for preparing at least one fatty amidoalkyldialkylamine by reacting at least one fatty acid containing from 8 to 24 carbon atoms with at least one dialkylaminoalkylamine of formula (I):

(I)

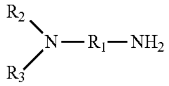

in which: $R_1$ represents a divalent alkyl group containing from 2 to 6 carbon atoms; $R_2$ and $R_3$ represent, independently of each other, monovalent alkyl groups-containing from 1 to 4 carbon atoms, using a molar ratio of said dialkylaminoalkylamine to said fatty acid of more than 1 and up to 1.5, in a presence of *Candida antarctica* lipase as a catalyst, wherein the reaction is carried out under vacuum at a pressure ranging from $25*10^2$ to $200*10^2$ Pa.

2. The method of claim 1, wherein the at least one fatty acid contains from 10 to 20 carbon atoms.

3. The method of claim 2, wherein the at least one fatty acid contains from 12 to 18 carbon atoms.

4. The method of claim 1, wherein the at least one fatty acid is chosen from lauric acid, stearic acid, oleic acid, and mixtures thereof, as well as mixtures of fatty acids comprising from 8 to 18 carbon atoms.

5. The method of claim 4, wherein the at least one fatty acid is chosen from lauric acid and stearic acid.

6. The method of claim 1, wherein in formula (I), $R_1$ represents a divalent alkyl group containing 3 or 4 carbon atoms.

7. The method of claim 1, wherein in formula (I), the $R_2$ and $R_3$ groups are identical.

8. The method of claim 7, wherein in formula (I), the $R_2$ and $R_3$ groups both represent methyl groups.

9. The method of claim 1, wherein the dialkylaminoalkylamine of formula (I) is dimethylaminopropyl amine.

10. The method of claim 1, wherein the molar ratio of dialkylaminoalkylamine(s) to fatty acid(s) ranges from 1.05 to 1.3.

11. The method of claim 10, wherein the molar ratio of dialkylaminoalkylamine(s) to fatty acid(s) ranges from 1.1 to 1.2.

12. The method of claim 1, wherein the catalyst is in a form of a solid catalyst containing *Candida Antarctica* lipase grafted onto a polymeric support.

13. The method of claim 12, wherein the polymeric support is an anionic resin.

14. The method of claim 13, wherein the anionic resin is an acrylic resin.

15. The method of claim 1, wherein *Candida Antarctica* lipase is present in an amount ranging from 0.2 to 2% by weight, with regard to a total weight of fatty acid(s).

16. The method of claim 15 wherein *Candida Antarctica* lipase is present in an amount ranging from 0.5 to 1.5% by weight, with regard to the total weight of fatty acid(s).

17. The method of claim 1, wherein the reaction is carried out at a temperature within the range from 75 to 120° C.

18. The method of claim 1, wherein the reaction is carried out in a batch reactor.

19. The method of claim 18, wherein after a first reaction cycle, the catalyst is recycled to the batch reactor where it is reused for a next reaction batch.

* * * * *